United States Patent [19]

Sundeen et al.

[11] 4,327,111

[45] Apr. 27, 1982

[54] N-SUBSTITUTED MERCAPTOACYL PRIPIONAMIDES

[75] Inventors: Joseph E. Sundeen, Yardley, Pa.; Tamara Dejneka, Skillman, N.J.

[73] Assignee: E. R. Squibb & Sons, Inc., Princeton, N.J.

[21] Appl. No.: 168,933

[22] Filed: Jul. 14, 1980

[51] Int. Cl.³ ............... A61K 31/335; C07D 323/02; A61K 31/265; A61K 31/16

[52] U.S. Cl. .................. 424/278; 424/301; 424/320; 424/324; 260/455 R; 564/192; 564/189; 564/190; 564/191; 564/162; 260/340.9 R

[58] Field of Search ............ 260/455 R, 340.9; 564/192, 189, 190, 191, 162; 424/278, 301, 320, 324

[56] References Cited

U.S. PATENT DOCUMENTS 4,105,776   8/1978   Ondetti et al. .................. 260/455 R

FOREIGN PATENT DOCUMENTS 1989   5/1979   European Pat. Off. ........ 260/455 R

*Primary Examiner*—John M. Ford
*Assistant Examiner*—Robert C. Whittenbaugh
*Attorney, Agent, or Firm*—Lawrence S. Levinson; Donald J. Barrack

[57] ABSTRACT

Mammalian collagenase is inhibited by compounds having the formula

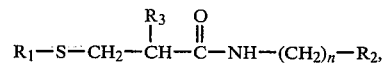

or a salt thereof, wherein $R_1$ is hydrogen, alkanoyl of 2 to 10 carbon atoms, or arylcarbonyl;

$R_2$ is 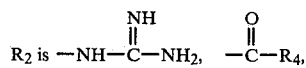 , 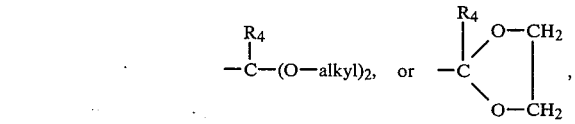 , wherein $R_4$ is hydrogen, alkyl or aryl;

$R_3$ is alkyl of 3 to 8 carbon atoms, cycloalkyl of 3 to 7 carbon atoms, aryl or arylalkyl; and n is an integer of 1 to 20.

16 Claims, No Drawings

N-SUBSTITUTED MERCAPTOACYL PRIPIONAMIDES

RELATED APPLICATIONS

United States patent applications Ser. No. 51,915, now U.S. Pat. No. 4,235,885 filed June 25, 1979 and Ser. No. 121,352, now U.S. Pat. No. 4,297,275 filed Feb. 14, 1980 disclose mammalian collagenase inhibitors having the formula $$R_a-S-CH_2-\underset{\underset{(CH_3)_2-CH-CH_2}{|}}{CH}-\overset{O}{\overset{\|}{C}}-R_b,$$

wherein $R_a$ is hydrogen or alkanoyl of 2 to 10 carbon atoms; $R_b$ is hydroxy, amino or $$-NH-(CH_2)_m-\underset{\underset{R_c}{|}}{CH}-\overset{O}{\overset{\|}{C}}-R_d;$$

$R_c$ is hydrogen, alkyl of 1 to 4 carbon atoms, $$-(CH_2)_3-N\overset{NH}{\overset{\|}{H}}CNH_2, \text{ or } -(CH_2)_2-\overset{O}{\overset{\|}{C}}-NH_2;$$

$R_d$ is hydroxy, amino, arginine, leucine, glutamine, alanine or glycine; and m is 0 or an integer of 1 to 9.

United States patent application Ser. No. 154,748, now U.S. Pat. No. 4,263,293 filed May 30, 1980 discloses mammalian collagenase inhibitors having the formula $$R_e-S-CH_2-\underset{\underset{R_f}{|}}{CH}-\overset{O}{\overset{\|}{C}}-NH-(CH_2)_n-R_g$$

wherein $R_e$ is hydrogen, alkanoyl of 2 to 10 carbon atoms, or arylcarbonyl; $R_f$ is alkyl of 3 to 8 carbon atoms, cycloalkyl of 3 to 7 carbon atoms, aryl or arylalkyl; $R_g$ is 1-pyrrolidinyl, 1-piperidinyl, 4-morpholinyl, 1-piperazinyl, or 4-alkyl-1-piperazinyl; and n is an integer of 1 to 20.

BACKGROUND OF THE INVENTION

European Patent Application No. 1,989, published May 30, 1979, discloses compounds having the formula $$R_h-S-\underset{\underset{R_j}{|}}{(\overset{R_i}{\overset{|}{C}})_n}-\overset{O}{\overset{\|}{C}}-NR_kR_p$$
$$\downarrow$$
$$(O)_m$$

wherein the symbols are defined, inter alia, as follows: $R_h$ is hydrogen, m is 0, $R_i$ and $R_j$ are independently hydrogen, alkyl, cycloalkyl, arylalkyl or aryl, n is 1 to 17 and $R_k$ and $R_p$ are independently hydrogen, cycloalkyl, alkyl, arylalkyl, alkoxyalkyl, aryloxyalkyl, hydroxyalkyl, or $-Y-NR_qR_r$ wherein Y is alkyl of 1 to 4 carbons and $R_q$ and $R_r$ are independently hydrogen, alkyl or phenyl.

U.S. Pat. No. 4,105,776, issued Aug. 8, 1978 is representative of a large body of art dealing with mercaptoacylamino acids which are useful for the treatment of angiotensin related hypertension.

BRIEF DESCRIPTION OF THE INVENTION

Mammalian collagenase is inhibited by compounds having the formula $$R_1-S-CH_2-\underset{\underset{R_3}{|}}{\overset{*}{CH}}-\overset{O}{\overset{\|}{C}}-NH-(CH_2)_n-R_2. \quad\quad \text{I}$$

In formula I, and throughout the specification, the symbols are as defined below:

$R_1$ is hydrogen, alkanoyl (acetyl is preferred) or arylcarbonyl (benzoyl is preferred);

$R_2$ is $-NH-\overset{NH}{\overset{\|}{C}}-NH_2$, $-\overset{O}{\overset{\|}{C}}-R_4$, $-\underset{\underset{R_4}{|}}{C}-(O-\text{alkyl})_2$, or $-\underset{\underset{O-CH_2}{\diagdown}}{\overset{\overset{R_4}{|}}{\underset{\diagup}{C}}}\overset{O-CH_2}{\underset{|}{\diagup}}$, wherein $R_4$ is hydrogen, alkyl or aryl;

$R_3$ is alkyl of 3 to 8 carbon atoms, cycloalkyl of 3 to 7 carbon atoms, aryl or arylalkyl; and n is an integer of 1 to 20.

The term "aryl", as used throughout the specification, either individually or as part of a larger group, refers to phenyl or phenyl substituted with one, two or three alkyl, alkoxy, halogen, amino, hydroxy, or alkanoyloxy groups. Phenyl and monosubstituted phenyl are the preferred aryl groups.

The terms "alkyl" and "alkoxy", as used throughout the specification (unless otherwise defined), either individually or as part of a larger group, refer to groups having 1 to 8 carbon atoms.

The term "alkanoyl", as used throughout the specification (unless otherwise defined), either individually or as part of a larger group, refer to groups having 2 to 10 carbon atoms.

The term halogen, as used throughout the specification, either individually or as part of a larger group, refers to fluorine, chlorine, bromine and iodine.

DETAILED DESCRIPTION OF THE INVENTION

The compounds of this invention can be prepared using as a starting material a carboxylic acid having the formula $$HO-CH_2-\underset{\underset{R_3}{|}}{CH}-\overset{O}{\overset{\|}{C}}-OH. \quad\quad \text{II}$$

Heating a carboxylic acid of formula II with phosphoric acid yields a compound having the formula $$CH_2=\underset{\underset{R_3}{|}}{C}-\overset{O}{\overset{\|}{C}}-OH, \quad\quad \text{III}$$

which can in turn be reacted with a thio acid having the formula

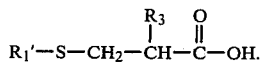   IV wherein $R_1'$ is alkanoyl or arylcarbonyl, to yield a product having the formula

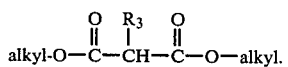   V

An acid of formula V, or ester thereof, can be coupled with a compound having the formula $$NH_2-(CH_2)_n-R_2,$$   VI or a salt thereof, to yield the compounds of formula I wherein $R_1$ is other than hydrogen. The coupling reaction can be effected by first activating the acid of formula V, e.g., by formation of a mixed or symmetrical anhydride, acid chloride, or active ester, or by the use of Woodward reagent K, EEDQ (N-ethoxycarbonyl-2-ethoxy-1,2-dihydroxyquinoline) or the like. A preferred method of activation comprises first treating an acid of formula V with an organic base (e.g., triethylamine) and then adding ethyl chloroformate.

Those products of formula I wherein $R_1$ is hydrogen can be prepared from corresponding compounds of formula I wherein $R_1$ is alkanoyl or arylcarbonyl by treatment of the acylthio compound with concentrated ammonium hydroxide.

Alternatively, the compounds of this invention can be prepared using as a starting material a malonic acid ester derivative having the formula

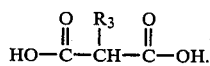   VII

Hydrolysis of a malonic acid ester derivative of formula VII yields the corresponding compound having the formula

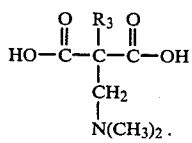   VIII

Sequential reaction of a diacid of formula VIII with a secondary amine (such as dimethylamine) and formaldehyde yields the corresponding compound having the formula

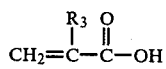   IX

Conversion of a compound of formula IX to the corresponding compound having the formula $$\begin{array}{c} R_3 \ O \\ | \ \ || \\ CH_2=C-C-OH \end{array}$$   III can be accomplished by melting the precursor compound. The compounds of this invention can be prepared from the compounds of formula III using the procedures described above.

Those compounds of formula I wherein $R_2$ is

can alternatively be prepared from the corresponding product of formula I wherein $R_2$ is

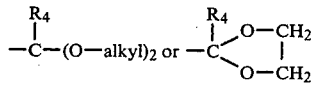

by acid hydrolysis.

The compounds of formula I have at least one asymmetric carbon atom; the carbon noted with an asterik (*) in formula I. The compounds accordingly exist in stereomeric forms or as racemic mixtures thereof. All of these are within the scope of this invention. The above described synthesis can utilize the starting compounds in the form of a racemic mixture or as a stereomer.

In mammals, collagenase is one of the key enzymes involved in the cartilage and joint destruction of rheumatoid arthritis; see, for example, *Arthritis and Rheumatism*, 20 (6):1231 (1977). It is, therefore, desirable to inhibit the action of the collagenase enzyme.

While not limiting the scope of this invention to a specific theory or mechanism of operation, it is nevertheless helpful to an understanding of the invention to review the possible reasons for the activity of the compounds of formula I. The main components of cartilage are the collagen polypeptide molecules. These polypeptides are cleaved by mammalian collagenase at a single site. The compounds of this invention resemble the susceptible sequence of the collagen molecules and, it is theorized, bind to the mammalian collagenase enzyme and inhibit its activity.

The mammalian collagenase enzyme contains zinc, which assists in the cleavage of a glycine-leucine or glycine-isoleucine bond and contains an extended cleft which interacts with an extended portion of the collagen molecule. This molecule in turn contains arginine as the last homologous amino acid in the substrate sequence adjacent to the cleavage site, a sequence showing a high degree of homology among the various types of collagen molecules. The inhibitors of this invention make use of these features of the enzyme and make modifications to enhance binding to the mammalian collagenase molecule.

The action of mammalian collagenase has also been implicated as a causative factor in several other diseases in mammals. These diseases include periodontal disease, corneal ulceration, tumor invasiveness, and epidermolysis bullosa; see, for example, *American Journal of Pathology*, 92 (2):509 (1978) and *The New England Journal of Medicine*, 291 (13):652 (1974).

For use in the treatment of rheumatoid arthritis, the compounds of this invention can be administered to a mammal in need thereof either orally or by injection intraarticularly into the affected joint. The daily dosage for a 70 kilogram mammal will be in the range of about 10 milligrams to 1 gram.

The compounds of this invention can be formulated in compositions such as tablets, capsules or elixirs for oral administration or in sterile solutions or suspensions for parenteral administration. About 10 to 500 mg of a compound of formula I can be formulated with a pharmaceutically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Salts of the compounds of formula I wherein $R_2$ is

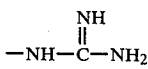

are also useful in the inhibition of mammalian collagenase and can be used and formulated following the procedures described above. The compounds of formula I wherein $R_2$ is

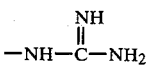

form acid-addition salts with organic and inorganic acids. These acid-addition salts are not only useful as inhibitors of mammalian collagenase but also frequently provide useful means for isolating the products from reaction mixtures by forming the salt in a medium in which it is insoluble, isolating the salt and then neutralizing the salt. Salts of the compounds of formula I wherein $R_2$ is

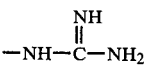

can also be formed by utilizing a salt of a compound of formula VI as a reactant.

The compounds of formula I wherein $R_3$ is 2-methylpropyl are preferred. Also preferred are those compounds of formula I wherein $R_1$ is hydrogen, acetyl or benzoyl. Also preferred are those compounds of formula I wherein n is 2, 3 or 4.

The following examples are specific embodiments of this invention.

EXAMPLE 1

N-(2,2-Dimethoxyethyl)-2-[(acetylthio)methyl]-4-methylpentanamide

(A) Isocaproic Acid

Potassium cyanide (28 g) is partly dissolved in 125 ml of ethanol and 30 ml of water. Amyl bromide (63.6 g) is added and the reaction mixture is digested on the steam cone for 24 hours. The solution is decanted from the potassium bromide on to 35 g of potassium hydroxide. This is digested on the steam cone for 20 hours, diluted with 50 ml of water and concentrated in vacuo to remove the ethanol. A 1:1 mixture of sulfuric acid and water is added to the reaction mixture and product is extracted with petroleum ether to yield 60.6 g of crude product. Vacuum distillation yields 43.4 g of product boiling at 90°–98° C./9 mm of Hg.

(B) 4-Methyl-2-(hydroxymethyl)pentanoic acid

Diisopropylamine (20.6 g) is dissolved in 80 ml of dry tetrahydrofuran. This solution is cooled to −30° C. n-Butyllithium (77 ml of 2.6 M in hexane) is added dropwise in a nitrogen atmosphere at a rate that maintains the reaction at −30° to −20° C., and this solution is stirred at −20° C. for 30 minutes. Isocaproic acid (11.6 g) in 10 ml of tetrahydrofuran is added dropwise at −20° to −10° C., then stirred at −10° C. for 30 minutes. In a separate flask, paraformaldehyde (28 g) is heated to about 200° C. and the vapors are carried in a stream of nitrogen over the surface of the tetrahydrofuran solution of the dilithium salt of isocaproic acid. During this procedure the temperature is kept between −10° and +10° C. After all of the paraformaldehyde has vaporized the reaction mixture is cooled to 0° C. and 10% hydrochloric acid is added dropwise until the reaction mixture becomes acidic. Product is extracted with 2 portions of ether (400 ml each). The ether is dried with magnesium sulfate, filtered and concentrated in vacuo to yield 13.2 g of crude material. Product is vacuum distilled to yield 9.0 g, boiling point 135°–142° C./9 mm of Hg.

(C) 4-Methyl-2-methylenepentanoic acid

4-Methyl-2-(hydroxymethyl)pentanoic acid (8.7 g) is heated with 10 drops of 85% phosphoric acid in a Wood's metal bath at 220° C. for 20 minutes. A distillation head is attached and the pressure is slowly decreased to 60 mm while the temperature is increased to 270° C. Product starts to distill and the pressure is further decreased to 10 mm. The vapor temperature varies between 180° and 190° C. The yield of the title compound as distillate is 7.0 g.

(D) 2-[(Acetylthio)methyl]-4-methylpentanoic acid

4-Methyl-2-methylenepentanoic acid (6.8 g) is stirred with 5 ml of thiolacetic acid under argon for 5 days, concentrated in vacuo and a portion is distilled. The product boils at 117°–120° C. at 9 mm of Hg.

(E) N-(2,2-Dimethoxyethyl)-2-[(acetylthio)methyl]-4-methylpentanamide

A solution of 2-[(acetylthio)methyl]-4-methylpentanoic acid (2.0 g) and triethyl amine (1.0 g) in 50 ml of tetrahydrofuran (THF) is cooled to −5° C. Ethyl chloroformate (1.1 g) in 5 ml of THF is added dropwise and the reaction mixture is stirred at −5° C. for 30 minutes. Amino acetaldehyde dimethyl acetal (1.1 g) in 20 ml of THF is added dropwise to the mixed anhydride solution at −5° C. After addition, it is stirred at 10°–20° C. for 2 hours and stored at 0° C. for about 16 hours. Triethylamine hydrochloride is filtered off and the filtrate is concentrated in vacuo. The residue (2.1 g) is dissolved in 3 ml of ether. Silica gel (5 g) is added and ether is evaporated off. This is placed on top of 40 g of dry silica gel and washed through with pentane, 1:1 pentane:ether and finally ether. Product elutes with ether to yield 1.3 g of product which solidifies to give a low melting waxy solid.

Anal. calc'd for $C_{13}H_{25}NO_4S \cdot 0.15 H_2O$: C, 53.09; H, 8.67; N, 4.76; S, 10.90. Found: C, 53.09; H, 8.73; N, 4.67; S, 10.89.

EXAMPLE 2

N-(2,2-Dimethoxyethyl)-2-(mercaptomethyl)-4-methylpentanamide

The N-(2,2-dimethoxyethyl)-2-[(acetylthio)methyl]-4-methylpentanamide obtained in Example 1 is dissolved in 15 ml of absolute ethanol and the atmosphere is purged with argon. Concentrated ammonium hydroxide (2 ml) is added and this solution is stirred at room temperature for 3 hours, concentrated to dryness in vacuo and dried at 50° C. for 8 hours over phosphorous pentoxide. The title compound (0.8 g) crystallizes, melting point 34°–37° C.

Anal. calc'd for $C_{11}H_{23}NO_3S.0.25H_2O$: C, 52.04; H, 9.33; N, 5.51; S, 12.63. Found: C, 52.09; H, 9.05; N, 5.64; S, 12.40.

EXAMPLE 3

N-[2-(Mercaptomethyl)-4-methylpentanoyl]amino acetaldehyde

The N-(2,2-dimethoxyethyl)-2-(mercaptomethyl)-4-methylpentanamide obtained in Example 2 is dissolved in 10 ml of water and treated with a few drops of 10% hydrochloric acid. After standing for 1 hour at 25° C., the water is removed in vacuo and the product is obtained as a powder by triturating with acetonitrile.

EXAMPLES 4–7

Following the procedures of Example 1 and 2 (sequentially), but substituting the compound listed in column I for amino acetaldehyde dimethyl acetal, yields the compound listed in column II, and on hydrolysis as in Example 3, the compound listed in column III.

(B) 4-[(Aminoiminomethyl)amino]butylamine, acetate (1:1)

A solution of agmatine sulfate (1.4 g) and sodium acetate (1.0 g) in 10 ml of water is concentrated in vacuo and the residue is slurried with hot absolute ethanol and filtered. The filtrate is evaporated and washed with ethyl acetate to give 1.5 g of the title compound, melting point 132°–136° C.

(C) 2-[(Acetylthio)methyl]-4-methyl-N-[4-[(aminoiminomethyl)amino]butyl]pentanamide, acetate (1:1)

The p-nitrophenyl ester of 2-[(acetylthio)methyl]-4-methylpentanoic acid (3.5 g) is dissolved in 75 ml of dimethylformamide, cooled to 5° C., and treated with a solution of the monoacetate salt of 4-[(aminoiminomethyl)amino]butylamine (1.6 g) in 10 ml of water. The mixture is stirred, for about 16 hours at 25° C., evaporated in vacuo leaving an aqueous solution and extracted thoroughly with ethyl acetate. The aqueous layer is lyophilized to a solid, which is washed with acetonitrile and dried in vacuo to give 2.8 g of the title compound.

EXAMPLE 9

2-(Mercaptomethyl)-4-methyl-N-[4-[(aminoiminomethyl)amino]butyl]pentanamide, acetate (1:1)

2-[(Acetylthio)methyl]-4-methyl-N-[4-[(aminoiminomethyl)amino]butyl]pentanamide, acetate (1:1) (1 g) is dissolved in 30 ml of water, cooled in ice, and purged with argon. Concentrated ammonium hydroxide (4 ml) is added, and the mixture is allowed to warm to 25° C. over 2 hours. The solution is lyophilized, and the resulting solid is triturated with acetonitrile. Drying in vacuo at 40° C. gives 0.8 g of the title compound.

EXAMPLES 10 AND 11

Following the procedures of Examples 8 and 9 (sequentially), but substituting the compound listed in column I for the monoacetate salt of 4-[(aminoiminomethyl)amino]butylamine, yields the acetate salt of the compound listed in column II.

EXAMPLE 8

2-[(Acetylthio)methyl]-4-methyl-N-[4-[(aminoiminomethyl)amino]butyl]pentanamide, acetate (1:1)

(A) 2-[(Acetylthio)methyl]-4-methylpentanoic acid, p-nitrophenyl ester

2-[(Acetylthio)methyl]-4-methylpentanoic acid (5.1 g, see Example 1D) in 100 ml of ethyl acetate is cooled to 5° C. and treated with p-nitrophenol (3.5 g) followed by 5.1 g of dicyclohexylcarbodiimide, in portions. After stirring for four hours at 5° C., the dicyclohexylurea is filtered and the ethyl acetate is removed in vacuo. The resulting solid is washed with hexane to give the title compound, 8.0 g, as an oil.

| Column I | Column II |
|---|---|
| 10. H$_2$N—CH$_2$—CH$_2$—NH—C(=NH)—NH$_2$ | HS—CH$_2$—CH(CH$_2$CH(CH$_3$)$_2$)—C(=O)—NH—CH$_2$—CH$_2$—NH—C(=NH)—NH$_2$ |
| 11. H$_2$N—(CH$_2$)$_7$—NH—C(=NH)—NH$_2$ | HS—CH$_2$—CH(CH$_2$CH(CH$_3$)$_2$)—C(=O)—NH—(CH$_2$)$_7$—NH—C(=NH)—NH$_2$ |

What is claimed is:

1. A compound having the formula $$R_1-S-CH_2-CH(R_3)-C(=O)-NH-(CH_2)_n-R_2,$$

or a salt thereof, wherein

R$_1$ is hydrogen, alkanoyl, or arylcarbonyl;

R$_2$ is —NH—C(=NH)—NH$_2$,  —C(=O)—R$_4$, $$-C(R_4)(O-alkyl)_2, \text{ or } -C(R_4)\begin{pmatrix}O-CH_2\\O-CH_2\end{pmatrix},$$

wherein R$_4$ is hydrogen, alkyl or aryl;

R$_3$ is alkyl of 3 to 8 carbon atoms, cycloalkyl of 3 to 7 carbon atoms, aryl or arylalkyl; and n is an integer of 1 to 20;

wherein the term "aryl" refers to phenyl or phenyl substituted; with 1, 2 or 3 alkyl, alkoxy, halogen, amino, hydroxy or alkanoyloxy groups; the terms "alkyl" and "alkoxy" refer to groups having 1 to 8 carbon atoms; and the term "alkanoyl" refers to groups having 2 to 10 carbon atoms.

2. A compound in accordance with claim 1 wherein R$_1$ is hydrogen.

3. A compound in accordance with claim 1 wherein R$_1$ is alkanoyl of 2 to 10 carbon atoms.

4. A compound in accordance with claim 1 wherein R$_1$ is arylcarbonyl.

5. A compound in accordance with claim 1 wherein R$_2$ is $$-NH-C(=NH)-NH_2.$$

6. A compound in accordance with claim 1 wherein R$_2$ is $$-C(=O)-R_4.$$

7. A compound in accordance with claim 1 wherein R$_2$ is $$-C(R_4)(O-alkyl)_2.$$

8. A compound in accordance with claim 6 wherein R$_4$ is hydrogen.

9. A compound in accordance with claim 7 wherein R$_4$ is hydrogen.

10. A compound in accordance with claim 1 wherein n is 2, 3 or 4.

11. A compound in accordance with claim 1 wherein R$_3$ is 2-methylpropyl.

12. The compound in accordance with claim 1 N-(2,2-dimethoxyethyl)-2-[(acetylthio)methyl]-4-methylpentanamide.

13. The compound in accordance with claim 1 N-(2,2-dimethoxyethyl)-2-(mercaptomethyl)-4-methylpentanamide.

14. The compound in accordance with claim 1 2-[(acetylthio)methyl]-4-methyl-N-[4-[(aminoiminomethyl)amino]butyl]pentanamide, acetate (1:1).

15. The compound in accordance with claim 1 2-(mercaptomethyl)-4-methyl-N-[4-[(aminoiminomethyl)amino]butyl]pentanamide, acetate (1:1).

16. A method for reducing the adverse effects of mammalian collagenase in a host mammal in need thereof, which comprises administering to said mammal an effective amount of a compound having the formula $$R_1-S-CH_2-CH(R_3)-C(=O)-NH-(CH_2)_n-R_2,$$

or a salt thereof, wherein R$_1$ is hydrogen, alkanoyl, or arylcarbonyl;

R$_2$ is —NH—C(=NH)—NH$_2$,  —C(=O)—R$_4$, $$-C(R_4)(O-alkyl)_2, \text{ or } -C(R_4)\begin{pmatrix}O-CH_2\\O-CH_2\end{pmatrix},$$

wherein R$_4$ is hydrogen, alkyl or aryl;

R$_3$ is alkyl of 3 to 8 carbon atoms, cycloalkyl of 3 to 7 carbon atoms, aryl or arylalkyl; and n is an integer of 1 to 20;

wherein the term "aryl" refers to phenyl or phenyl substituted; with 1, 2 or 3 alkyl, alkoxy, halogen, amino, hydroxy or alkanoyloxy groups; the terms "alkyl" and "alkoxy" refer to groups having 1 to 8 carbon atoms; and the term "alkanoyl" refers to groups having 2 to 10 carbon atoms.

* * * * *

UNITED STATES PATENT AND TRADEMARK OFFICE
CERTIFICATE OF CORRECTION

PATENT NO. : 4,327,111
DATED : April 27, 1982
INVENTOR(S) : Joseph E. Sundeen, et al.

It is certified that error appears in the above—identified patent and that said Letters Patent is hereby corrected as shown below:

Column 1, in the title, correct the spelling of the word
--PROPIONAMIDES--

Signed and Sealed this

Twenty-fourth Day of May 1983

[SEAL]

Attest:

DONALD J. QUIGG

Attesting Officer  Acting Commissioner of Patents and Trademarks